(12) United States Patent
Nandy

(10) Patent No.: US 10,900,015 B2
(45) Date of Patent: Jan. 26, 2021

(54) PROCESS FOR IMPROVED FERMENTATION OF A MICROORGANISM

(71) Applicant: UNIBO A/S, Odense M (DK)

(72) Inventor: Subir Kumar Nandy, Kongens Lyngby (DK)

(73) Assignee: UNIBIO A/S, Roskilde (DK)

( * ) Notice: Subject to any disclaimer, the term of this patent is extended or adjusted under 35 U.S.C. 154(b) by 160 days.

(21) Appl. No.: 15/774,658

(22) PCT Filed: Nov. 8, 2016

(86) PCT No.: PCT/EP2016/076950
§ 371 (c)(1),
(2) Date: May 9, 2018

(87) PCT Pub. No.: WO2017/080987
PCT Pub. Date: May 18, 2017

(65) Prior Publication Data
US 2018/0327710 A1 Nov. 15, 2018

(30) Foreign Application Priority Data
Nov. 9, 2015 (DK) .................................. 2015 00705

(51) Int. Cl.
*C12N 1/20* (2006.01)
*C12N 1/30* (2006.01)
*C12M 1/04* (2006.01)
*C12M 1/00* (2006.01)

(52) U.S. Cl.
CPC ................ *C12N 1/20* (2013.01); *C12M 1/04* (2013.01); *C12M 21/00* (2013.01); *C12N 1/30* (2013.01); *C12M 1/00* (2013.01); *C12M 29/06* (2013.01)

(58) Field of Classification Search
None
See application file for complete search history.

(56) References Cited

FOREIGN PATENT DOCUMENTS

| WO | 01/60974 | 8/2001 | |
|----|----------|--------|---|
| WO | 2015/120337 | 8/2015 | |
| WO | WO-2015120337 A1 * | 8/2015 | ............. C12P 7/065 |

OTHER PUBLICATIONS

Acha, V. et al., Biotechnol Lett 2002, pp. 675-679.*
Acha, V. et al., Biotechnol. Lett. 2002 vol. 24, pp. 675-679.*
International Search Report (ISA/EP), dated May 12, 2017, 6 pages.
Database WPI, Week 197407, Thomson Scientific, Long, GB; AN 1974-12254V XP002767957 & JP S48 88274 A (Agency of Ind. Sci & Technology) Nov. 19, 1973 abstract, 1 page.
Acha, V. et al.: "The absolute requirement for carbon dioxide for aerobic methane oxidation by a methanotrophic-heterotrophic soil community of bacteria", Biotechnology Letters, vol. 24, No. 9, May 2002, pp. 675-679, XP002767958.
Database WPI, Week 199642, Thomson Scientific, London, GB; AN 1996-423699 XP002767959, & RU 2 051 962 C1 (Volova T G) Jan. 10, 1996, 1 page.
Anonym.: "Commission Regulation (EU) No. 575/2011 of Jun. 16, 2011 on the Catalogue of feed materials" pp. 159/25-159/65.
Written Opinion of the ISA/EP, PCT/EP2016/076950, dated May 12, 2017, 25 pages.

* cited by examiner

*Primary Examiner* — Heidi Reese
(74) *Attorney, Agent, or Firm* — Ware, Fressola, Maguire & Barber LLP

(57) ABSTRACT

A method for improving biomass production and/or growth rate of a microorganism in a fermentation process is shown, and includes: (i) providing one or more microorganisms; (ii) providing a fermentation substrate suitable for fermenting the one or more microorganisms; (iii) mixing the one or more microorganisms and the fermentation substrate providing a fermentation broth; (iv) adding the fermentation broth to a fermentation tank; (v) injecting at least one gaseous substrate into the fermentation broth; (vi) running the fermentation process for a fermentation period of at least 1 hour; wherein the at least one gaseous substrate comprises one or more greenhouse gases, such as carbon dioxide ($CO_2$).

27 Claims, 1 Drawing Sheet

PROCESS FOR IMPROVED FERMENTATION OF A MICROORGANISM

TECHNICAL FIELD OF THE INVENTION

The present invention relates to a fermentation process for fermenting a microorganism. In particular the present invention relates to a fermentation process having an improved biomass production and an increased growth rate of a microorganism, such as a bacterial strain, e.g. a methanotrophic bacterial strain.

BACKGROUND OF THE INVENTION

A number of microorganisms, such as bacteria, have been known for the utilization of methane gas by fermentation. Typically methanotrophs consume methane as sole carbon and energy source. In this process, methane can be fed directly or from natural gas and for this purpose, a pure or co-culture bacterial consortium is necessary to support growth over longer periods in a continuous culture.

Traditionally, the production or fermentation of single cell protein (SCP) from natural gas or methane is using a single carbon source, namely methane, under the condition of an initial start-up time of 5-6 days before the onset of continuous cultivation. Traditionally, the biomass production achieved under steady state is around 1.5-2.5 g/L on a dry matter basis. In order to enhance the fermentation efficiency of traditional fermentation processes, the methane utilization process for the SCP production should be very efficient.

During traditional fermentation processes, such as fermentation processes involving methanotrophic bacterial strains, the microorganisms produce carbon dioxide ($CO_2$) which is released to the fermentation broth. Thus, $CO_2$ is traditionally considered a waste gas. Hence, in order to improve productivity of the fermentation process, traditional processes teach that $CO_2$ is to be removed from the fermentation tank, e.g. from the headspace of a U-loop reactor, in order to improve productivity.

Furthermore, construction costs and operating cost for the production of fermented protein sources, e.g. for animal feed, are rather high and at the same time there is increasing demands and requirements to quality, standard and regulation and a low price per kg protein. Hence, it is a challenge to establish a profitable business and even small improvements in efficiency, or reduced production costs may have significant influence on the income of the producer.

Hence, there is a need and interest in the industry for an improved fermentation process. In particular, there is a need in the industry for a more efficient, fermentation process which would result in an improved biomass production and an increased growth rate of a microorganism, such as a bacterial strain, e.g. a methanotrophic bacterial strain, without compromising the requirements and demands of the industry.

SUMMARY OF THE INVENTION

Thus, an object of the present invention relates to a fermentation process for fermenting a microorganism.

In particular, it is an object of the present invention to provide a fermentation process having an improved biomass production and an increased growth rate of a microorganism, such as a bacterial strain, e.g. a methanotrophic bacterial strain.

Thus, one aspect of the invention relates to a method for improving biomass production and/or growth rate of a microorganism in a fermentation process, said method comprises the steps of:
(i) Providing one or more microorganism;
(ii) Providing a fermentation substrate suitable for fermenting the one or more microorganism;
(iii) Mixing the one or more microorganism and the fermentation substrate providing a fermentation broth;
(iv) Adding the fermentation broth to a fermentation tank;
(v) injecting at least one gaseous substrate into the fermentation broth;
(vi) Running the fermentation process for a fermentation period of at least 1 hour;
wherein the at least one gaseous substrate comprises one or more greenhouse gases, such as carbon dioxide ($CO_2$).

Another aspect of the present invention relates to a method for improving biomass production and/or growth rate of a microorganism in a fermentation process, said method comprises the steps of:
(i) Providing one or more microorganism;
(ii) Providing a fermentation substrate suitable for fermenting the one or more microorganism;
(iii) Mixing the one or more microorganism and the fermentation substrate providing a fermentation broth;
(iv) Adding the fermentation broth to a fermentation tank;
(v) injecting at least one gaseous substrate into the fermentation broth;
(vi) Running the fermentation process for a fermentation period of at least 1 hour;
wherein the at least one gaseous substrate comprises the combination of two or more carbon sources.

Yet another aspect of the present invention relates to a fermentation tank comprising an inlet for injecting at least one gaseous substrate into the fermentation tank, wherein the at least one gaseous substrate comprises carbon dioxide ($CO_2$).

Still another aspect of the present invention relates to a composition comprising one or more microorganisms obtainable by the method according to the present invention.

Figure 1A:
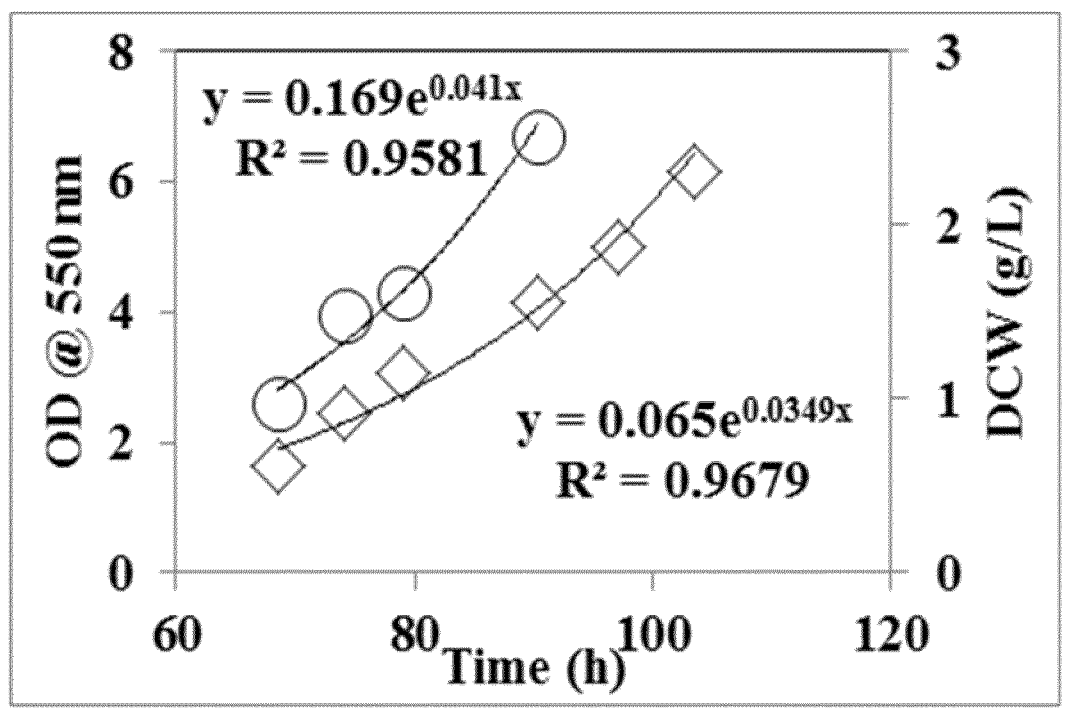
FIG. 1 shows *M. capsulatus* grown in 1 L fermentation tank (a) using a traditional method using methane FIG. 1a, or using a combination of methane and $CO_2$, as the carbon source. The continuous cultivation was started after a minimum of 4-5 days, normally an average of 7-8 days, of batch growth using a dilution rate of 0.05 $h^{-1}$. Dry cell weight (open squares) and the culture's optical density (open density) at 550 nm (OD550) measurement shows a specific growth rate of maximum approximately 0.04 $h^{-1}$, and on an average of 0.025. The biomass concentration at steady state is on an average of 1.5-2.5 g/L, data not shown, and (b) using the fermentation process according to the present invention. The continuous cultivation was started after only 1 day due to the high specific growth rate (approximately 0.16 $h^{-1}$; —based on dry cell weight and OD550 data) and a dilution rate of 0.05 $h^{-1}$ was used. The steady state biomass concentration was at least 4 g/L, data not shown.

The present invention will now be described in more detail in the following.

DETAILED DESCRIPTION OF THE INVENTION

Accordingly, the present invention relates to a fermentation process which has been developed for the fermentation of a microorganism, such as a bacterial strain, e.g. a methanotrophs bacterial strain of the family Methylococcaceae or Methylocystaceae, which is cultivated in a fermenter containing a carbon source, a nitrogen source, and inorganic salts. The process may be a semi aerobic process (SAP). The fermentation process may result in at least 4 times higher growth rate than traditional fermentation processes and/or at least 1.5 times higher biomass production. The inventors of the present invention surprisingly found that carbon dioxide had a significant influence on the improved biomass production and the increased growth rate obtained from the present invention. Hence, the process of the present invention not only shows a significant improvement in the protein production (demonstrated by the improved biomass production and the increased growth rate) for near future food requirement, but the present invention also demonstrate itself to be effective on reducing pollution of the environment since the fermentation process involves consumption of greenhouse gasses, such as $CO_2$.

Hence, a preferred embodiment of the present invention relates to a method for improving biomass production and/or growth rate of a microorganism in a fermentation process, said method comprises the steps of:
(i) Providing one or more microorganism;
(ii) Providing a fermentation substrate suitable for fermenting the one or more microorganism;
(iii) Mixing the one or more microorganism and the fermentation substrate providing a fermentation broth;
(iv) Adding the fermentation broth to a fermentation tank;
(v) injecting at least one gaseous substrate into the fermentation broth;
(vi) Running the fermentation process for a fermentation period of at least 1 hour;
wherein the at least one gaseous substrate comprises one or more greenhouse gases, such as carbon dioxide ($CO_2$).

In an embodiment of the present invention, the gaseous substrate further comprises an alkane, preferably, the alkane is a C1 compound.

A further preferred embodiment of the present invention relates to a method for improving biomass production and/or growth rate of a microorganism in a fermentation process, said method comprises the steps of:
(i) Providing one or more microorganism;
(ii) Providing a fermentation substrate suitable for fermenting the one or more microorganism;
(iii) Mixing the one or more microorganism and the fermentation substrate providing a fermentation broth;
(iv) Adding the fermentation broth to a fermentation tank;
(v) injecting at least one gaseous substrate into the fermentation broth;
(vi) Running the fermentation process for a fermentation period of at least 1 hour;
wherein the at least one gaseous substrate comprises the combination of two or more carbon sources.

In an embodiment of the present invention the at least one gaseous substrate may comprise one or more greenhouse gases, such as carbon dioxide ($CO_2$).

In another embodiment of the present invention the gaseous substrate comprises at least 0.05% carbon dioxide, such as at least 0.075% carbon dioxide, e.g. at least 0.1% carbon dioxide, such as at least 0.2% carbon dioxide, e.g. at least 0.3% carbon dioxide, such as at least 0.4% carbon dioxide, e.g. at least 0.5% carbon dioxide, such as at least 0.6% carbon dioxide, e.g. at least 0.7% carbon dioxide, such as at least 0.8% carbon dioxide, e.g. at least 0.9% carbon dioxide, such as at least 1.0% carbon dioxide, e.g. at least 1.25% carbon dioxide, such as at least 1.5% carbon dioxide, e.g. at least 1.75% carbon dioxide, such as at least 2.0% carbon dioxide, e.g. at least 2.5% carbon dioxide, such as at least 3.0% carbon dioxide, e.g. at least 3.5% carbon dioxide, such as at least 4.0% carbon dioxide, e.g. at least 4.5% carbon dioxide, such as at least 5.5% carbon dioxide, e.g. at least 6.0% carbon dioxide, such as at least 6.5% carbon dioxide, e.g. at least 7.0% carbon dioxide, such as at least 7.5% carbon dioxide, e.g. at least 8.0% carbon dioxide.

The gaseous substrate, and the greenhouse gasses, e.g. $CO_2$, may be injected into the fermentation broth. Preferably, the amount of gaseous substrate, and the greenhouse gasses, e.g. $CO_2$, injected into the fermentation broth is at least 0.001 L/min/L fermentation broth, such as at least 0.005 L/min/L fermentation broth, e.g. at least 0.01 L/min/L fermentation broth, such as at least 0.05 L/min/L fermentation broth, e.g. at least 0.1 L/min/L fermentation broth, such as at least 0.13 L/min/L fermentation broth, e.g. at least 0.15 L/min/L fermentation broth, such as at least 0.2 L/min/L fermentation broth, e.g. at least 0.25 L/min/L fermentation broth, such as at least 0.3 L/min/L fermentation broth, e.g. at least 0.4 L/min/L fermentation broth, such as at least 0.5 L/min/L fermentation broth, e.g. at least 0.60 L/min/L fermentation broth, such as at least 0.7 L/min/L fermentation broth, e.g. at least 0.75 L/min/L fermentation broth.

In a further embodiment of the present invention the combination of two or more carbon sources comprise the combination of one or more greenhouse gases, such as carbon dioxide ($CO_2$) with one or more alkane.

The alkane may preferably be a C1 compound and/or a C1 alkane. Preferably the C1 compound and/or the C1 alkane may be methane, methanol, natural gas, biogas, syngas or any combination hereof. Even more preferably, the C1 compound and/or the C1 alkane may be methane.

In an embodiment of the present invention the gaseous substrate comprises a ratio between the carbon dioxide and the alkane of 1 part carbon dioxide to about 1 parts alkane on a weight:weight basis, such as 1 part carbon dioxide to about 1.5 parts alkane, 1 part carbon dioxide to about 2 parts alkane, 1 part carbon dioxide to about 2.5 parts alkane, 1 part carbon dioxide to about 3 parts alkane.

The gaseous substrate further comprises at least one nitrogen source. Preferably at least one nitrogen source may be selected from the group consisting of ammonia, nitrate, molecular nitrogen, and a combination hereof. Preferably, the nitrogen source is a combination of ammonia and nitrate.

The gaseous substrate may further comprise oxygen. Preferably, the oxygen may be provided as atmospheric air, pure oxygen, or air enriched with oxygen.

In an embodiment of the present invention the gaseous substrate may have a content of oxygen, preferably, atmospheric air, in the range of 2-15 times higher (vol/vol) than the content of C1 alkane, preferably, methane; such as 3-12 times higher (vol/vol); e.g. 4-10 times higher (vol/vol); such as 5-9 times higher (vol/vol); e.g. 6-8 times higher (vol/vol).

In another embodiment of the present invention the gaseous substrate may have a content of oxygen, preferably, atmospheric air, is in the range of 5-25 times higher (vol/vol) than the content of greenhouse gases, preferably, carbon dioxide; such as 7-20 times higher (vol/vol); e.g. 9-15 times higher (vol/vol); such as 10-14 times higher (vol/vol); e.g. 11-13 times higher (vol/vol).

In the present context the term "fermentation substrate" relates to a liquid, preferably, an aqueous, medium comprising the soluble components necessary for the microorganism to growth.

During the fermentation process the carbon source, the nitrogen source and/or the oxygen source is provided in the gaseous substrate. In order to make the carbon source, the nitrogen source and/or the oxygen source to become readily available to the microorganisms during the fermentation process the gaseous substrate should be made soluble in the fermentation broth.

Gas bubbles in liquids have a tendency to fuse together to larger bubbles (coalesce) and to avoid the coalescence of the gas bubbles, mixers, such as static gas mixers or baffles, may be provided for re-dispersion of the gases in the fermentation broth.

The amount of gas, which may advantageously be dispersed in the liquid, may depend on the hydrostatic pressure. In the case of tall reactors, it will therefore be advantageous to have several locations for the introduction of gases in the down-flow part. Preferably, at least one static mixing element may be placed at a distance from or immediately after each inlet for dispersing the gas in the fermentation broth.

Mixing of the one or more microorganism and the fermentation substrate providing a fermentation broth may be done at outside the fermentation tank or inside the fermentation tank. In an embodiment of the present invention the mixing of the one or more microorganism and the fermentation substrate providing a fermentation broth may be done in the fermentation tank.

In an embodiment of the present invention the fermentation process may be a batch fermentation, a fed batch, or a continuous fermentation process. Preferably, the fermentation process may be a continuous fermentation process.

In a further embodiment of the present invention the continuous fermentation process may be conducted as a chemostat, pH-stat, productstat or other continuous fermentation process modes.

In a preferred embodiment of the present invention the fermentation process is conducted in an airlift reactor (the fermentation tank being an airlift reactor), a loop-reactor (the fermentation tank being a loop-reactor), a U-shape reactor (the fermentation tank being an U-shape reactor) and/or a stirred tank reactor (the fermentation tank being a stirred tank reactor).

In an embodiment the fermentation broth may be subjected to mixing. Preferably, the fermentation tank comprises one or more mixers suitable for mixing the fermentation broth. In an embodiment of the present invention the fermentation tank comprises at least one mixer in close connection to, preferably, downstream from, a gaseous inlet for introducing the gaseous substrate.

One way to increase the solubility of the gaseous substrate in the fermentation broth is by increasing the hydrostatic pressure. In an embodiment of the present invention the pressure of the fermentation broth and the gaseous substrate is increase to an over pressure relative to the pressure outside the fermentation tank of at least 1.5 bar; such as at least 1.75 bar; e.g. at least 2.0 bar; such as at least 2.5 bar; e.g. at least 3.0 bar; such as at least 3.5 bar; e.g. at least 4.0 bar; such as at least 4.5 bar; e.g. at least 5.0 bar; such as at least 5.5 bar; e.g. at least 6.0 bar; such as at least 7.0 bar; e.g. at least 8.0 bar; such as at least 9.0 bar; e.g. at least 10.0 bar.

The combination of the various fermentation conditions is dependent on the microorganism to growth in the fermentation tank.

The microorganism is selected from the group consisting of bacterial cell, fungal cell, algae cell, or animal cell. Preferably, the microorganism may be a bacterial cell.

In an embodiment of the present invention the bacterial cell may be a methanotrophic bacterial cell.

In yet an embodiment of the present invention the bacterial cell may be a methanotrophic bacterial cell selected from a *Methylococcus* strain.

In an even further embodiment of the present invention the *Methylococcus* strain may be *Methylococcus capsulatus*.

In even a further embodiment of the present invention, the bacterial cell (preferably, when grown in the presence of natural gas) is selected from *M. capsulatus; Alcaligen acidovorans* (preferably NCIMB 13287); *Bacillus firmus* (preferably NCIMB 13280); and/or *Aneurobacillus danicus* (preferably NCIMB 13288). Preferably, bacterial cell is a combination of *M. capsulatus; Alcaligen acidovorans* (preferably NCIMB 13287); *Bacillus firmus* (preferably NCIMB 13280); and *Aneurobacillus danicus* (preferably NCIMB 13288).

In a preferred embodiment of the present invention, the fermentation may be started using a combination of carbon dioxide ($CO_2$) and (a) methanotrophic bacteria and methane or (b) methanotrophic bacteria, *Alcaligen acidovorans* (preferably NCIMB 13287); *Bacillus firmus* (preferably NCIMB 13280); and/or *Aneurobacillus danicus* (preferably NCIMB 13288) and natural gas. Following this stating procedure the fermentation may be continues as a steady state fermentation where the carbon source is natural gas, *Alcaligen acidovorans* (preferably NCIMB 13287); *Bacillus firmus* (preferably NCIMB 13280); and/or *Aneurobacillus danicus* (preferably NCIMB 13288) are added if not added earlier, and without the additional addition of $CO_2$.

As mentioned previously the method according to the present invention results in an improved biomass production and an increased growth rate of the microorganism, such as a bacterial strain, e.g. a methanotrophic bacterial strain.

In a preferred embodiment of the present invention the method of the present invention provides a microbial growth rate during the fermentation process of at least $0.04\ h^{-1}$, e.g. at least $0.05\ h^{-1}$, such as at least $0.06\ h^{-1}$, e.g. at least $0.08\ h^{-1}$, such as at least $0.10\ h^{-1}$, e.g. at least $0.12\ h^{-1}$, such as at least $0.14\ h^{-1}$, e.g. at least $0.15\ h^{-1}$, such as at least $0.16\ h^{-1}$, e.g. at least $0.17\ h^{-1}$, such as at least $0.18\ h^{-1}$, e.g. at least $0.19\ h^{-1}$, such as at least $0.20\ h^{-1}$, e.g. at least $0.22\ h^{-1}$, such as at least $0.25\ h^{-1}$, e.g. at least $0.27\ h^{-1}$, such as at least $0.30\ h^{-1}$, e.g. at least $0.32\ h^{-1}$, such as at least $0.35\ h^{-1}$, e.g. at least $0.37\ h^{-1}$.

In another preferred embodiment of the present invention a biomass production of at least 2.5 g/l on a dry-matter basis may be provided, such as a biomass production of at least 2.6 g/l on a dry-matter basis may be provided, e.g. a biomass production of at least 2.7 g/l on a dry-matter basis may be provided, such as a biomass production of at least 2.8 g/l on a dry-matter basis may be provided, e.g. a biomass production of at least 2.9 g/l on a dry-matter basis may be provided, such as a biomass production of at least 3.0 g/l on a dry-matter basis may be provided, e.g. a biomass production of at least 3.5 g/l on a dry-matter basis may be provided, such as a biomass production of at least 4.0 g/l on a dry-matter basis is provided, e.g. a biomass production of at least 4.5 g/l on a dry-matter basis may be provided, such as a biomass production of at least 5.0 g/l on a dry-matter basis may be provided, e.g. a biomass production of at least 5.5 g/l on a dry-matter basis may be provided, such as a biomass production of at least 6.0 g/l on a dry-matter basis may be provided, e.g. a biomass production of at least 6.5 g/l on a dry-matter basis may be provided, such as a biomass production of at least 7.0 g/l on a dry-matter basis may be provided, e.g. a biomass production of at least 7.5 g/l on a dry-matter basis may be provided, such as a biomass production of at least 10.0 g/l on a dry-matter basis may be provided, e.g. a biomass production of at least 12.5 g/l on a dry-matter basis may be provided, such as a biomass production of at least 15.0 g/l on a dry-matter basis may be provided, e.g. a biomass production of at least 17.5 g/l on a dry-matter basis may be provided, such as a biomass production of at least 20.0 g/l on a dry-matter basis may be provided, e.g. a biomass production of at least 22.5 g/l on a dry-matter basis may be provided, such as a biomass production of at least 25.0 g/l on a dry-matter basis may be provided, e.g. a biomass production of at least 27.5 g/l on a dry-matter basis may be provided such as a biomass production of at least 30.0 g/l on a dry-matter basis may be provided.

The inventors of the present invention found, in addition to the improved biomass production and the increased growth rate that the high biomass production (or the maximum biomass production (in terms of g/l on a dry-matter basis) may be obtained significantly faster than traditional methods. Thus, in an embodiment of the present invention the high biomass production (or the maximum biomass production (in terms of g/l on a dry-matter basis) may be obtained in less than 5 days, such as in less than 4 days, e.g. in less than 3 days, such as in less than 2 days, e.g. in less than 24 hours, such as in less than 20 hours, e.g. in less than 16 hours, such as in less than 14 hours, e.g. in less than 12 hours, such as in less than 10 hours, e.g. in less than 8 hours.

In an embodiment of the present invention a biomass production of at least 3.5 g/l on a dry-matter basis is provided with in less than 24 hours, such as a biomass production of at least 4.0 g/l on a dry-matter basis is provided with in less than 20 hours, e.g. a biomass production of at least 4.5 g/l on a dry-matter basis is provided with in less than 14 hours, such as a biomass production of at least 5.0 g/l on a dry-matter basis is provided with in less than 10 hours, e.g. a biomass production of at least 5.5 g/l on a dry-matter basis is provided with in less than 8 hours.

In order to provide the new method according to the present invention a new fermentation tank has been developed. Thus, in a preferred embodiment of the present invention a fermentation tank is provided. The fermentation tank comprises an inlet for injecting at least one gaseous substrate into the fermentation tank, wherein the at least one gaseous substrate comprises carbon dioxide ($CO_2$).

In a preferred embodiment of the present invention the fermentation tank is an airlift reactor, a loop-reactor, a U-shape reactor, or a stirred tank reactor.

To improve the amount of dissolved gasses (dissolved gaseous substrate) the fermentation tank according to the present invention may further comprise one or more mixing devices. Preferably, the one or more mixing devices may be a static mixing device, or baffles and/or an active mixing device.

For further improving the fermentation process the fermentation tank may further comprises one or more sensor. Said sensors may be suitable for determine gasses (such as $CO_2$, methane, oxygen, etc.), nutrition, minerals, pH, etc.

In an embodiment of the present invention the one or more sensor comprises a $CO_2$ sensor.

In a further embodiment of the present invention the one or more sensor comprises a sensor for determining dissolved $CO_2$.

The method, according to the present invention, may be used for converting greenhouse gasses, such as $CO_2$, into biomass and/or proteins, and/or for reducing the content of greenhouse gasses, such as $CO_2$, in a medium.

It should be noted that embodiments and features described in the context of one of the aspects of the present invention also apply to the other aspects of the invention.

The invention will now be described in further details in the following non-limiting examples.

EXAMPLES

Example 1

The aim of example 1 is to demonstrate the improved biomass production and the increased growth rate obtained by the present invention. The fermentations are performed at both batch fermentation and steady state under continuous cultivation using a semi aerobic process compared to traditional processes.

Materials and Methods:

A strain of methanotrophic bacteria (*Methylococcus capsulatus*) was provided. This strain (NCIMB 11132) was provide from NCIMB (National Collection of Industrial, Food and Marine Bacteria, Aberdeen, Scotland) and was used throughout this present work for both fermentation processes according to the present invention and traditional fermentation processes. Three other strains *Alcaligen acidovorans* (NCIMB 13287), *Bacillus firmus* (NCIMB 13280) and *Aneurobacillus danicus* (NCIMB 13288) were also provide and used in this study together with *M. capsulatus* when natural gas was used as carbon source.

For the method according to the present invention the strains could be added directly to the fermentation process (added as glycerol stock), and continuous cultivation could be started after only 1 day of batch fermentation, whereas the traditional fermentation, using the same inoculums size, was cultivated for at least 5-7 days in batch phase before the mode was switch to continuous cultivation.

The carbon sources used were methane (experiment 1A), methane and $CO_2$ (experiment 1B), or natural gas and $CO_2$ (experiment 1c).

The nitrogen sources used in the experiments used are nitrate, ammonia or ammonium nitrate.

The cultivations performed in the experiments (according to the method of the present invention and the traditional method) were carried out in batch fermenters having a 1 L working volume of minimal medium in three biological replicates and continuous cultivation was started. The fermenters (the fermentation tanks) were autoclaved with part of the minimal medium components. After the other part of the minimal medium, autoclaved separately, is added, the fermentation tanks were inoculated with 5% washed pre-culture.

The aeration rate was 1.5 volume of air per volume of culture suspension per min (vvm). The methane flow was 0.36 L/min for the traditional experiment 1a and experiment 1b had a methane flow of 0.23 L/min, and experiment 1c has a 0.29 L/min natural gas flow for the method according to the present invention. For the method according the present invention 0.145 L/min of $CO_2$ was injected for experiment 1c, and 0.13 L/min of $CO_2$ was injected for experiment 1b. pH of the medium was kept at 6.8 by the automatic addition of 2 N NaOH or 2 N $H_2SO_4$, and the temperature was kept at 42° C. throughout the cultivations. Dissolved oxygen calibration was performed by gassing with air and $N_2$. The agitation speed was maintained at 600 revolutions per minute (rpm). Dilution rate during the continuous cultivation was 0.05 $h^{-1}$.

Results

| Experiment | Carbon source/s | Nitrogen source | | μ | a | b |
|---|---|---|---|---|---|---|
| Experiment 1A (without $CO_2$) | $CH_4$ | $NaNO_3$ | Batch | 0.024 ± 0.0003 | 0.46 ± 0.003 | 0.003 ± 0.0002 |
| | | | SS | 0.05 | 1.27 ± 0.01 | 0.006 ± 0.0006 |
| | $CH_4$ | $NH_3$ | Batch | 0.024 ± 0.0003 | 0.18 ± 0.01 | 0.001 ± 0 |
| | | | SS | 0.05 | 1.41 ± 0.005 | 0.007 ± 2.52E−05 |
| | $CH_4$ | $NH_4NO_3$ | Batch | 0.024 ± 0.0007 | 0.15 ± 0.008 | 0.001 ± 5.77E−05 |
| | | | SS | 0.05 | 1.27 ± 0.002 | 0.007 ± 2.85E−05 |
| Experiment 1B (with $CH_4 + CO_2$) | $CH4 + CO_2$ | $NaNO3$ | Batch | 0.16 ± 0.003 | 0.67 ± 0.003 | 0.05 ± 0.003 |
| | | | SS | 0.05 | 1.66 ± 0.01 | 0.06 ± 0.002 |
| | $CH_4 + CO_2$ | $NH_3$ | Batch | 0.16 ± 0.005 | 0.59 ± 0.002 | 0.05 ± 0.001 |
| | | | SS | 0.05 | 1.52 ± 0.002 | 0.06 ± 0.001 |
| | $CH_4 + CO_2$ | $NH_4NO_3$ | Batch | 0.16 ± 0.004 | 0.44 ± 0.0013 | 0.04 ± 0.0006 |
| | | | SS | 0.05 | 1.52 ± 0.005 | 0.06 ± 7.58E−05 |
| Experiment 1C (with natural gas + $CO_2$) | $NG + CO_2$ | $NaNO_3$ | Batch | 0.16 ± 0.0016 | 0.68 ± 0.013 | 0.05 ± 0.0009 |
| | | | SS | 0.05 | 2.05 ± 0.002 | 0.09 ± 0.004 |
| | $NG + CO_2$ | $NH_3$ | Batch | 0.16 ± 0.0017 | 0.69 ± 0.0023 | 0.05 ± 0.0013 |
| | | | SS | 0.05 | 1.95 ± 0.0013 | 0.09 ± 0.0001 |
| | $NG + CO_2$ | $NH_4NO_3$ | Batch | 0.16 ± 0.002 | 0.68 ± 0.005 | 0.05 ± 0.0001 |
| | | | SS | 0.05 | 1.93 ± 0.001 | 0.09 ± 0.0007 |

| Experiment | Carbon source/s | Nitrogen source | | c | d | e |
|---|---|---|---|---|---|---|
| Experiment 1A (without $CO_2$) | $CH_4$ | $NaNO_3$ | Batch | 0 | 0.05 ± 0.0015 | 0.1 ± 0.006 |
| | | | SS | 0 | 0.05 ± 0.005 | 0.04 ± 0.004 |
| | $CH_4$ | $NH_3$ | Batch | 0 | 0.03 ± 0.0001 | 0.03 ± 0.003 |
| | | | SS | 0 | 0.06 ± 0.0002 | 0.05 ± 0.0006 |
| | $CH_4$ | $NH_4NO_3$ | Batch | 0 | 0.03 ± 0.001 | 0.04 ± 0.002 |
| | | | SS | 0 | 0.06 ± 0.0003 | 0.05 ± 0.0003 |
| Experiment 1B (with $CH_4 + CO_2$) | $CH4 + CO_2$ | $NaNO3$ | Batch | 0.47 ± 0.018 | 0.77 ± 0.005 | 0 |
| | | | SS | 0.03 ± 0.003 | 0.18 ± 0.003 | 0 |
| | $CH_4 + CO_2$ | $NH_3$ | Batch | 0.39 ± 0.03 | 0.68 ± 0.04 | 0 |
| | | | SS | 0.06 ± 0.001 | 0.18 ± 0.003 | 0 |
| | $CH_4 + CO_2$ | $NH_4NO_3$ | Batch | 0.35 ± 0.008 | 0.5 ± 0.013 | 0 |
| | | | SS | 0.07 ± 0.003 | 0.18 ± 0.001 | 0 |
| Experiment 1C (with natural gas + $CO_2$) | $NG + CO_2$ | $NaNO_3$ | Batch | 0.34 ± 0.025 | 0.85 ± 0.017 | 0 |
| | | | SS | 0.03 ± 0.004 | 0.3 ± 0.013 | 0 |
| | $NG + CO_2$ | $NH_3$ | Batch | 0.36 ± 0.021 | 0.79 ± 0.02 | 0 |
| | | | SS | 0.04 ± 0.008 | 0.27 ± 0.0006 | 0 |
| | $NG + CO_2$ | $NH_4NO_3$ | Batch | 0.35 ± 0.005 | 0.68 ± 0.007 | 0 |
| | | | SS | 0.04 ± 0.0055 | 0.28 ± 0.0025 | 0 |

This table illustrates the experimental values from biological cultivations by *M. capsulatus* alone or the triplicate cultivations of *M. capsulatus* in combination with *Alcaligen acidovorans* (NCIMB 13287), *Bacillus firmus* (NCIMB 13280) and *Aneurobacillus danicus* (NCIMB 13288). SS means steady state fermentation. Batch means batch fermentation.

The letters a, b, c, d, and e relates to the stoichiometry coefficients of the respective compounds in mol per mol of methane consumption. The Letter "p" relates to the specific growth rate.

DISCUSSION

A theoretical stoichiometry of the chemical conversion provided during the fermentation can be written as follows:

$$CH_4 + \underline{a}O_2 + \underline{b}NaNO_3/NH_3/NH_4NO_3 + \underline{c}CO_2 \rightarrow \underline{d}CH_{1.8}O_{0.5}N_{0.2} + \underline{e}CO_2 + \underline{f}H_2O$$

$CH_4$ is methane; $O_2$ is Oxygen; $NaNO_3$ is Sodium nitrate; $NH_3$ is Ammonia; $NH_4NO_3$ is Ammonium nitrate; $CO_2$ is Carbon dioxide; $CH_{1.8}O_{0.5}N_{0.2}$ is biomass; and $H_2O$ is water.

The letters $\underline{a}$, $\underline{b}$, $\underline{c}$, $\underline{d}$, $\underline{e}$ and $\underline{f}$ relates to the stoichiometry coefficients of the respective compounds in mol per mol of methane consumption.

A theoretical stoichiometry balance has been performed for the process with or without Carbon dioxide ($CO_2$) under different nitrogen sources.

This table illustrates the theoretical values for different stoichiometry based on different carbon and nitrogen sources:

| Process | Carbon source/s | Nitrogen source | a | b | c | d* | e | f |
|---|---|---|---|---|---|---|---|---|
| Without $CO_2$ | $CH_4$ | $NaNO_3$ | 1.22 | 0.104 | 0 | 0.52 | 0.48 | 1.532 |
| | $CH_4$ | $NH_3$ | 1.45 | 0.104 | 0 | 0.52 | 0.48 | 1.69 |
| | $CH_4$ | $NH_4NO_3$ | 1.35 | 0.052 | 0 | 0.52 | 0.48 | 1.64 |
| With $CO_2$ | $CH_4 + CO_2$ | $NaNO_3$ | 1.22 | 0.104 | 0.13 | 0.52 | 0.61 | 1.532 |
| | $CH_4 + CO_2$ | $NH_3$ | 1.454 | 0.104 | 0.247 | 0.52 | 0.727 | 1.688 |
| | $CH_4 + CO_2$ | $NH_4NO_3$ | 0.65 | 0.052 | 0.195 | 0.52 | 0.675 | 1.532 |

*It is assumed that the biomass yield over methane consumption – the yield coefficient (d) is 0.52 (mol/mol).

*M. capsulatus* was grown alone or together with the 3 other stains of bacteria (*Alcaligen acidovorans* (NCIMB 13287), *Bacillus firmus* (NCIMB 13280) and *Aneurobacillus danicus* (NCIMB 13288)), in 2 different conditions (with $CO_2$ (the method of the present invention) or without $CO_2$ (the traditional methods)), and with different types of nitrogen sources (nitrate, ammonia or ammonium nitrate) in a specific minimal medium. The optical density and dry cell weight of biomass as well as consumption of methane and carbon dioxide ($CO_2$) were monitored every 2-3 hours in the batch phase in the method of the present invention. Due to the slower growth, the sampling frequency is lower for the traditional process where $CO_2$ is absent. The growth rate achieved from the process without using $CO_2$, shows no improvements and it took at least 6 days to grow (not shown) whereas using a carbon source, such as natural gas, together with $CO_2$ resulted in much faster growth with a maximum specific growth rate of 0.16 $h^{-1}$ (see the result table). The same result was also achieved from a U-loop fermenter of 100 L working volume.

Figure 1B:
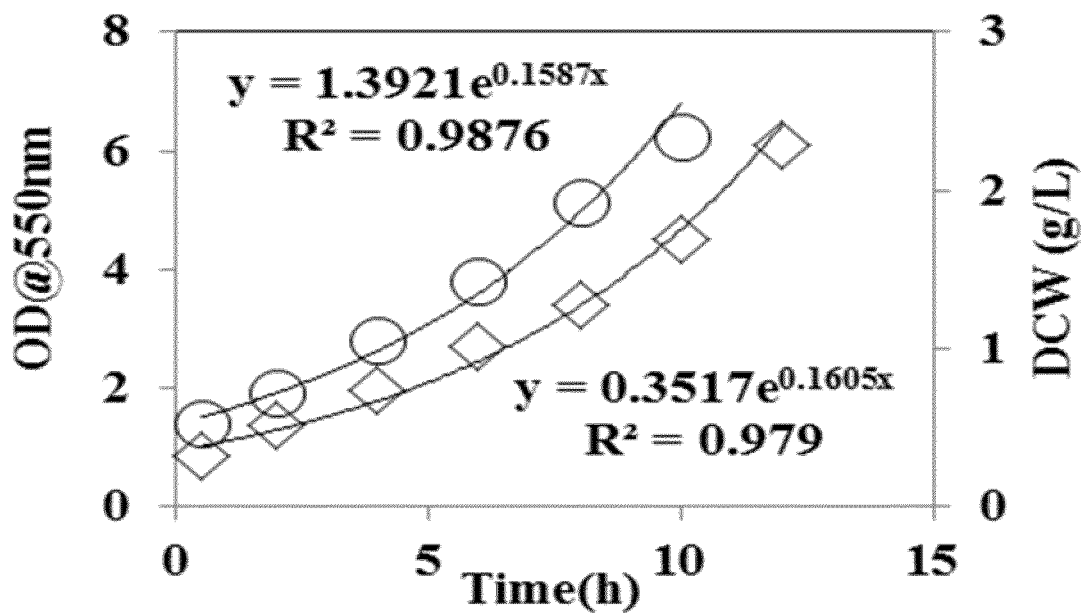

FIG. 1 shows *M. capsulatus* growths in 1 L fermentation tank (a) using a traditional method using methane as the sole carbon source. The continuous cultivation was started after 4-5 days of batch growth using a dilution rate of 0.05 $h^{-1}$. Dry cell weight and the culture's optical density at 550 nm (OD550) measurement shows a specific growth rate of approximately 0.04 $h^{-1}$, The biomass concentration at steady state is 2-2.5 g/L, data not shown, and (b) using the fermentation process according to the present invention. The continuous cultivation was started after only 1 day due to the high specific growth rate (approximately 0.16 $h^{-1}$; based on dry cell weight and OD550 data) and a dilution rate of 0.05 $h^{-1}$ was used. The steady state biomass concentration was 4 g/L, data not shown.

The results clearly demonstrate that cultivation of the microorganisms, such as methanotrophic bacteria (methylococcaceae), e.g. *M. capsulatus* under the addition of $CO_2$ according to the present invention, may be significantly improved and that the production costs per gram protein may be significantly decreased, compared the to the traditional fermentation processes.

The invention claimed is:

1. A method for improving biomass production, growth rate or both, of a microorganism in a fermentation process, said method comprising:
   (i) Providing one or more microorganism, wherein the one or more microorganism comprise methanotrophic bacteria;
   (ii) Providing a fermentation substrate suitable for fermenting the one or more microorganism;
   (iii) Mixing the one or more microorganism and the fermentation substrate providing a fermentation broth;
   (iv) Adding the fermentation broth to a fermentation tank;
   (v) Continuously injecting at least one gaseous substrate into the fermentation broth;
   (vi) Running the fermentation process for a fermentation period of at least 1 hour;
   wherein the at least one gaseous substrate comprises carbon dioxide ($CO_2$) wherein the amount of $CO_2$ injected into the fermentation broth is at least 0.001 L/min/L fermentation broth.

2. The method according to claim 1, wherein the gaseous substrate further comprises a C1 compound.

3. A method for improving biomass production, growth rate, or both, of a microorganism in a fermentation process, said method comprising:
   (i) Providing one or more microorganism, wherein the one or more microorganism comprise methanotrophic bacteria;
   (ii) Providing a fermentation substrate suitable for fermenting the one or more microorganism,
   (iii) Mixing the one or more microorganism and the fermentation substrate providing a fermentation broth;
   (iv) Adding the fermentation broth to a fermentation tank;
   (v) Continuously injecting at least one gaseous substrate into the fermentation broth;
   (vi) Running the fermentation process for a fermentation period of at least 1 hour;
   wherein the at least one gaseous substrate comprises a combination of two or more carbon sources.

4. The method according to claim 3, wherein the combination of two or more carbon sources comprises a combination of methane and $CO_2$.

5. The method according to claim 1, wherein the mixing of the one or more microorganism and the fermentation substrate providing a fermentation broth is done in the fermentation tank.

6. The method according to claim 1, wherein the fermentation broth is subjected to mixing.

7. The method according to claim 1, wherein the fermentation process is conducted in an airlift reactor, a loop-reactor, a U-shape reactor, or a stirred tank reactor.

8. The method according to claim 1, wherein a pressure of the fermentation broth and the gaseous substrate is increased to an over pressure relative to the pressure outside the fermentation tank of at least 1.5 bar.

9. The method according to claim 1, wherein the methanotrophic bacteria is selected from a *Methylococcus*.

10. The method, according to claim 1, wherein the fermentation process is a batch fermentation, a batch fed, or a continuous fermentation process.

11. The method according claim 1, wherein the continuous fermentation process is conducted as a chemostat, pH-stat, productstat or other continuous fermentation process modes.

12. The method according to claim 1, wherein the gaseous substrate comprises at least 0.05% carbon dioxide.

13. The method according to claim 2, wherein the compound is an alkane.

14. The method according to claim 2, wherein the C1 compound is methane, methanol, natural gas or any combination thereof.

15. The method according to claim 14, wherein the gaseous substrate comprises a ratio between the carbon dioxide and the alkane of 1 part carbon dioxide to 1 to 3 parts alkane on a weight:weight basis.

16. The method according to claim 1, wherein the gaseous substrate further comprises at least one nitrogen source.

17. The method according to claim 16, wherein the at least one nitrogen source is selected from the group consisting of ammonia, nitrate, molecular nitrogen, and a combination thereof.

18. The method according to claim 1, wherein the gaseous substrate further comprises oxygen.

19. The method according to claim 18, wherein the oxygen is provided as atmospheric air, pure oxygen, or air enriched with oxygen.

20. The method according to claim 19, wherein the gaseous substrate has a content of oxygen, in a range of 2-15 times higher (vol/vol) than a C1 alkane content of the gaseous substrate.

21. The method according to claim 18, wherein the gaseous substrate has a content of oxygen in a range of 5-25 times higher (vol/vol) than $CO_2$ content.

22. The method according to claim 1, wherein the microbial growth rate during the fermentation process is at least 0.04 $h^{-1}$.

23. The method according to claim 1, wherein a biomass production of at least 2.5 g/l on a dry-matter basis is provided.

24. The method according to claim 23 wherein the biomass production is obtained in less than 5 days.

25. The method according to claim 1, wherein a biomass production of at least 3.5 g/l on a dry-matter basis is provided within less than 2.4 hours.

26. A method for improving biomass production, growth rate, or both, of a microorganism in a fermentation process, said method comprising:
(i) Providing one or more microorganism;
(ii) Providing a fermentation substrate suitable for fermenting the one or more microorganism;
(iii) Mixing the one or more microorganism and the fermentation substrate providing a fermentation broth;
(Iv) Adding the fermentation broth to a fermentation tank-,
(v) Continuously injecting at least one gaseous substrate into the fermentation broth;
(vi) Running the fermentation process for a fermentation period of at least 1 hour;

wherein the at least one gaseous substrate comprises carbon dioxide ($CO_2$), wherein the amount of $CO_2$ injected into the fermentation broth is at least 0.001 L/min/L fermentation broth and wherein the gaseous substrate comprises a C1 compound and the C1 compound is methane, methanol, natural gas or any combination thereof, wherein the microorganism is selected from the group consisting of bacterial cell, fungal cell, algae cell, and animal cell, and wherein the microorganism is a bacterial cell, wherein the bacterial cell is a methanotrophic bacterial cell.

27. The method according to claim 26, wherein the methanotrophic bacterial cell is selected from a *Methylococcus*.

* * * * *